US012733875B2

(12) United States Patent
Furman et al.

(10) Patent No.: US 12,733,875 B2
(45) Date of Patent: Sep. 15, 2026

(54) TECHNIQUES FOR EXPERIMENTAL PROGRAMS USING DATA FROM WEARABLE DEVICE

(71) Applicant: Oura Health Oy, Oulu (FI)

(72) Inventors: Laura Furman, San Francisco, CA (US); Quynh Nguyen, San Francisco, CA (US); Sally Chan, Brooklyn, NY (US); Janne Käki, Helsinki (FI); Dmitrii Aleksandrov, Vantaa (FI); Damian Winiarczuk, Cracow (PL); Marcin Banaszynski, Rybnik (PL); Mika Erkkilä, Oulu (FI); Geoffrey Koops, San Francisco, CA (US); Jake Harris Sherman, Portland, OR (US); Ivan Uladzimiravich Markevich, Espoo (FI); Lauren Maymar, Belvedere, CA (US)

(73) Assignee: Oura Health Oy, Oulu (FI)

( * ) Notice: Subject to any disclaimer, the term of this patent is extended or adjusted under 35 U.S.C. 154(b) by 187 days.

(21) Appl. No.: 18/489,506

(22) Filed: Oct. 18, 2023

(65) Prior Publication Data

US 2024/0122544 A1 Apr. 18, 2024

Related U.S. Application Data

(60) Provisional application No. 63/417,243, filed on Oct. 18, 2022.

(51) Int. Cl.
*A61B 5/00* (2006.01)
*A61B 5/026* (2006.01)
(Continued)

(52) U.S. Cl.
CPC .......... *A61B 5/6826* (2013.01); *A61B 5/0261* (2013.01); *A61B 5/7267* (2013.01);
(Continued)

(58) Field of Classification Search
CPC ...... G16H 20/30; G16H 40/67; A61B 5/6826; A61B 5/0261; A61B 5/7267;
(Continued)

(56) References Cited

U.S. PATENT DOCUMENTS

2004/0220637 A1* 11/2004 Zdeblick ............ A61B 5/14539 607/17
2021/0379388 A1* 12/2021 Connor .............. A61M 60/531
(Continued)

*Primary Examiner* — Sana Sahand
(74) *Attorney, Agent, or Firm* — ArentFox Schiff LLP

(57) ABSTRACT

Methods, systems, and devices for experimental programs are described. A method includes acquiring baseline PPG data from a user via a wearable device throughout a time interval, and displaying one or more experimental programs via a user device based on the baseline PPG data, where each experimental program is associated with one or more behavioral changes. Upon a selection of an experimental program, the method includes acquiring additional PPG data from the user via the wearable device throughout a time interval of the experimental program. The method includes identifying adherence of the user to a behavioral change of the experimental program based on the additional PPG data and/or information received via the user device. The method further includes displaying, via the user device, changes between the baseline PPG data and the additional PPG data based on identifying the adherence to the behavioral change.

20 Claims, 9 Drawing Sheets

(51) Int. Cl.
*G16H 20/30* (2018.01)
*G16H 40/67* (2018.01)

(52) U.S. Cl.
CPC .......... *A61B 5/7435* (2013.01); *A61B 5/7475* (2013.01); *G16H 20/30* (2018.01); *G16H 40/67* (2018.01); *A61B 5/0022* (2013.01)

(58) Field of Classification Search
CPC ... A61B 5/7435; A61B 5/7475; A61B 5/0022; A61B 5/02416; A61B 5/02438; A61B 5/681; A61B 5/165
See application file for complete search history.

(56) References Cited

U.S. PATENT DOCUMENTS

| | | | | |
|---|---|---|---|---|
| 2022/0040487 | A1* | 2/2022 | Burnam | G16H 10/60 |
| 2022/0282962 | A1* | 9/2022 | Burnam | G01B 5/008 |

* cited by examiner

800

TECHNIQUES FOR EXPERIMENTAL PROGRAMS USING DATA FROM WEARABLE DEVICE

CROSS REFERENCE

The present Application for Patent claims the benefit of U.S. Provisional Patent Application No. 63/417,243 by Furman et al., entitled "TECHNIQUES FOR EXPERIMENTAL PROGRAMS USING DATA FROM WEARABLE DEVICE," filed Oct. 18, 2022, which is assigned to the assignee hereof and expressly incorporated by reference herein.

FIELD OF TECHNOLOGY

The following relates to wearable devices and data processing, including techniques for experimental programs using data from wearable devices.

BACKGROUND

Some wearable devices may be configured to collect data from users associated with exercise, sleep, and the like. Some users may want to make behavioral changes to improve their sleep or overall health, but may not know what types of behavioral changes will positively or negatively affect their health.

DETAILED DESCRIPTION

Figure 1:
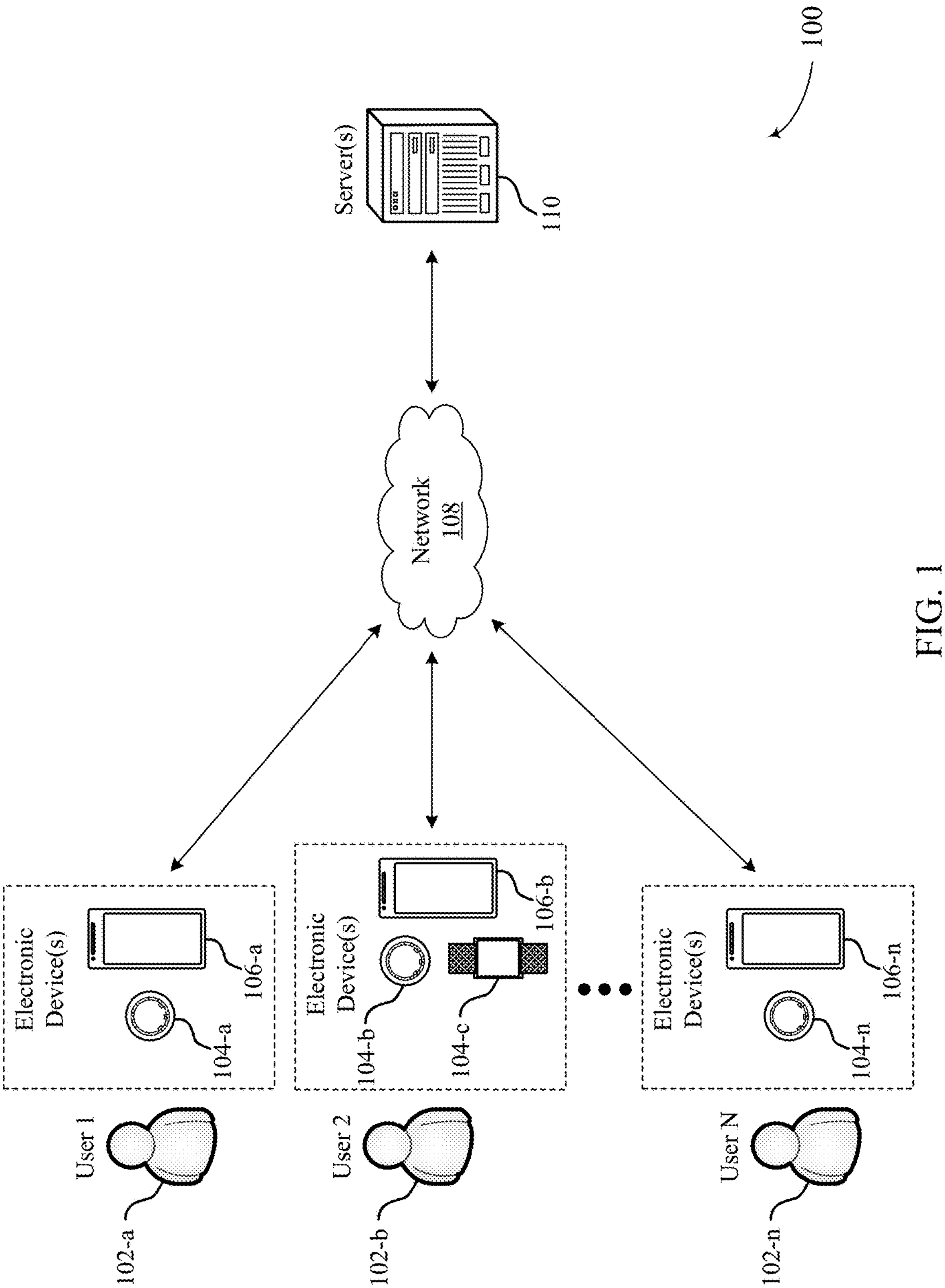
FIG. 1 illustrates an example of a system that supports techniques for experimental programs using data from wearable devices in accordance with aspects of the present disclosure.

Some wearable devices may be configured to collect physiological data from users associated with exercise, sleep, and the like. Some users may want to make behavioral changes to improve their sleep or overall health, but may not know what types of behavioral changes will positively or negatively affect their health. While there are many potential sources of information for making health-related decisions (e.g., medical journals, blogs, influencers, other users, etc.), users may be exposed to conflicting information regarding what types of behavioral changes they should make. For example, if a user wants to improve their sleep, some information may indicate that the user should avoid caffeine in the afternoon, while other information may indicate that the user should take a magnesium supplement. As such, conflicting information may make it difficult for users to make behavioral changes that positively affect their health.

Moreover, each user may respond to behavioral changes differently than others (e.g., some users may benefit from reduced caffeine, while caffeine may have little to no effect on other users). Additionally, even after deciding on a behavioral change, users may give up on the behavioral change after a short period of time and before any positive effects on their health may take place. Such lack of adherence to behavioral changes, such as diets, is particularly problematic for some users when they are unable to physically see the effect the behavioral change is making on their overall health. Further, upon making a behavioral change, most users have no way of quantifiably assessing the effect the behavioral change had on their health, and are therefore left to subjectively evaluate the behavioral change, which is oftentimes extremely unreliable and subject to the user's own biases.

Accordingly, aspects of the present disclosure are directed to "experimental programs" that utilize physiological data (e.g., photoplethysmogram (PPG) data) collected via a wearable device, where the experimental programs include behavioral changes that are intended to improve one or more aspects of the user's overall health. In particular, aspects of the present disclosure are directed to techniques for recommending experimental programs to users based on their physiological data and/or based on their health-related goals, and demonstrating to the user how the experimental programs could affect (or have affected) their overall health. Moreover, aspects of the present disclosure are directed to techniques for automatically determining whether or not (or to what extent) the users adhere to behavioral changes associated with the experimental programs, and showing the user what effect their level of adherence could affect (or has affected) changes to their overall health.

For example, a user may indicate a desire to improve their sleep efficiency. In this example, a system associated with a wearable device may recommend different experimental programs to the user that are associated with behavioral changes intended to improve the user's sleep efficiency. For example, one experimental program may include a program in which participating users refrain from consuming caffeine for six hours prior to their bedtime. Another experimental program may include a program in which participating users adjust their bedtime by a certain amount of time. Upon selecting an experimental program, the wearable device may collect physiological data from the user, and compare the acquired physiological data to the user's baseline physiological data (e.g., data collected prior to the experimental program). The physiological data from the user may be an example of PPG data, and the baseline physiological data may be an example of baseline PPG data.

In some cases, physiological data collected during the experimental program may be used to determine whether or not (or to what extent) the user is adhering to the experimental program (e.g., whether or not the user is refraining from consuming caffeine before bedtime, or whether the user is moving their bedtime up). Throughout the experimental program, and/or after a conclusion of the experimental program, the system may display information to the user that indicates how the experimental program affected one or more parameters of their physiological data (e.g., how the behavioral change affected their overall health). In this regard, techniques described herein may provide users with concrete, science-based answers regarding what types of behavioral changes (e.g., habits) positively or negatively affected their overall health.

In some cases, the system may recommend experimental programs based on what types of experimental programs resulted in positive changes for other users, such as other users with similar demographic information (e.g., similar baseline data, similar age, same gender, etc.). In some aspects, the system may estimate how a particular experimental program will affect a given user, such as based on the user's own baseline data and/or based on how other users responded to the experimental program. For instance, continuing with the example above, the system may state that the experimental program associated with restricted caffeine consumption is expected/estimated to improve the user's sleep efficiency by X %, where the experimental program associated with the adjusted bedtime is expected/estimated to improve the user's sleep efficiency by Y %. Such information may be useful to users when deciding what types of behavioral changes may be most beneficial to their own body type and physiological condition.

Aspects of the disclosure are initially described in the context of systems supporting physiological data collection from users via wearable devices. Additional aspects of the disclosure are described in the context of example graphical user interfaces (GUIs). Aspects of the disclosure are further illustrated by and described with reference to apparatus diagrams, system diagrams, and flowcharts that relate to techniques for experimental programs using data from wearable devices.

FIG. 1 illustrates an example of a system 100 that supports techniques for experimental programs using data from wearable devices in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as light-emitting diodes (LEDs) (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, PPG data, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for "experimental programs" that utilize physiological data (e.g., PPG data) collected via a wearable device 104, where the experimental programs include behavioral changes that are intended to improve one or more aspects of the user's overall health. In particular, aspects of the system 100 may support techniques for recommending experimental programs to users 102 based on their PPG data and/or based on their health-related goals, and demonstrating to the users 102 how the experimental programs could affect (or have affected) their overall health.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
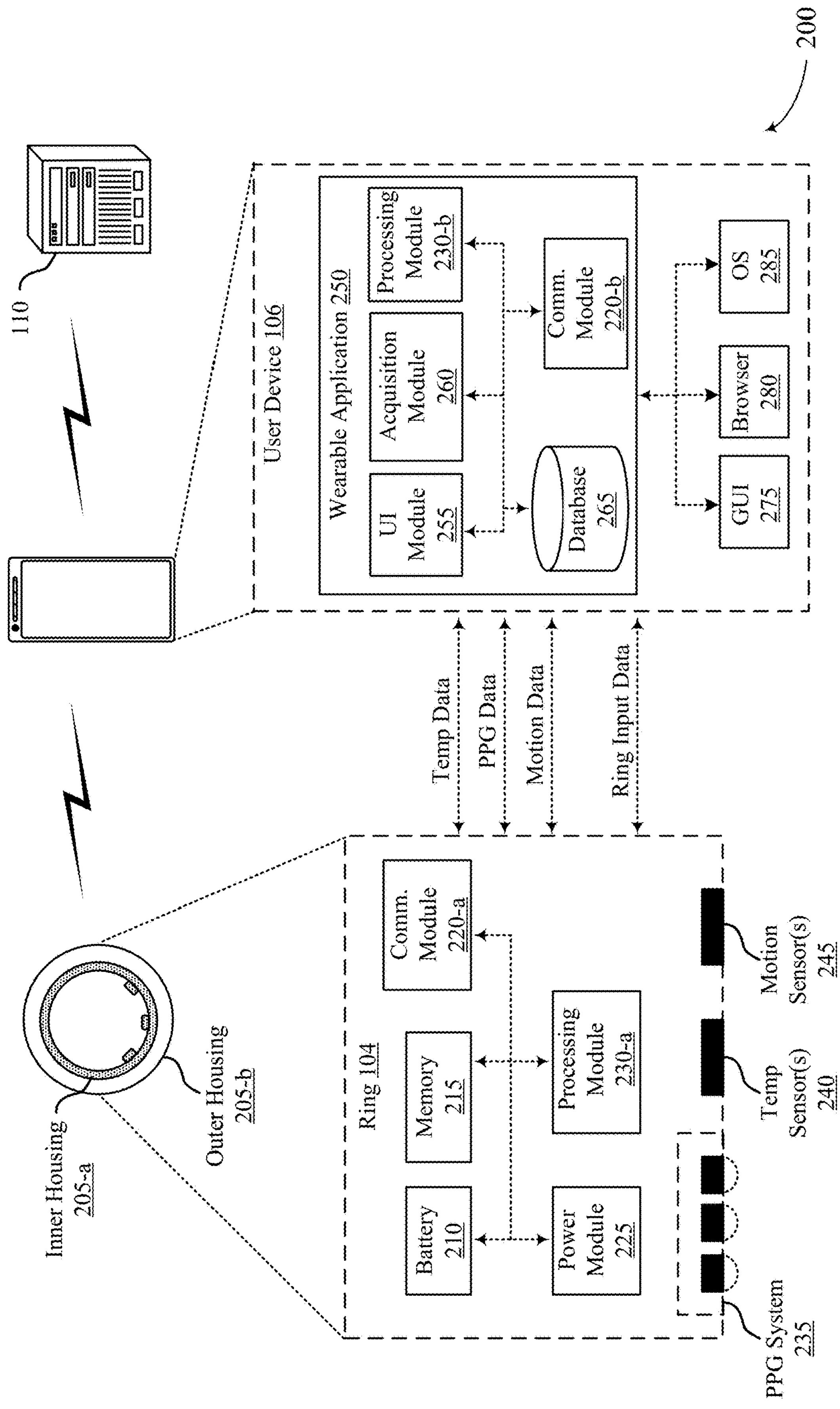
FIG. 2 illustrates an example of a system that supports techniques for experimental programs using data from wearable devices in accordance with aspects of the present disclosure.

FIG. 2 illustrates an example of a system 200 that supports techniques for experimental programs using data from wearable devices in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, that may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include LEDs. The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMl160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and Readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for "experimental programs" that utilize physiological data (e.g., PPG data) collected via a wearable device 104, where the experimental programs include behavioral changes that are intended to improve one or more aspects of the user's overall health. In particular, aspects of the system 100 may support techniques for recommending experimental programs to users 102 based on their PPG data and/or based on their health-related goals, and demonstrating to the users 102 how the experimental programs could affect (or have affected) their overall health.

In some cases, the system 200 may support techniques for identifying a user's level of adherence to a behavioral change associated with a respective experimental program based on data collected via the wearable device 104. In other words, physiological data collected via the wearable device 104 (and/or other sources of information, such as location information or "tags" inputted by the user) may be used to determine whether or not, or to what extent, the user adheres to a given behavioral change.

For example, a user may participate in an experimental program in which participating users refrain from drinking alcohol for two weeks. In this example, the user's level of adherence to the program may be based on how much and/or how frequently the user consumes alcohol during the two weeks of the program (e.g., more alcohol consumption results in lower adherence, less alcohol consumption results in higher adherence). In such cases, physiological data collected via the wearable device 104 and/or other data (e.g., user-inputted tags, location data, etc.) may be used to determine whether or not the user has consumed alcohol, and therefore may be used to determine the level of adherence to the experimental program.

Attendant advantages of the present disclosure may be further shown and described with reference to FIG. 3.

Figure 3:
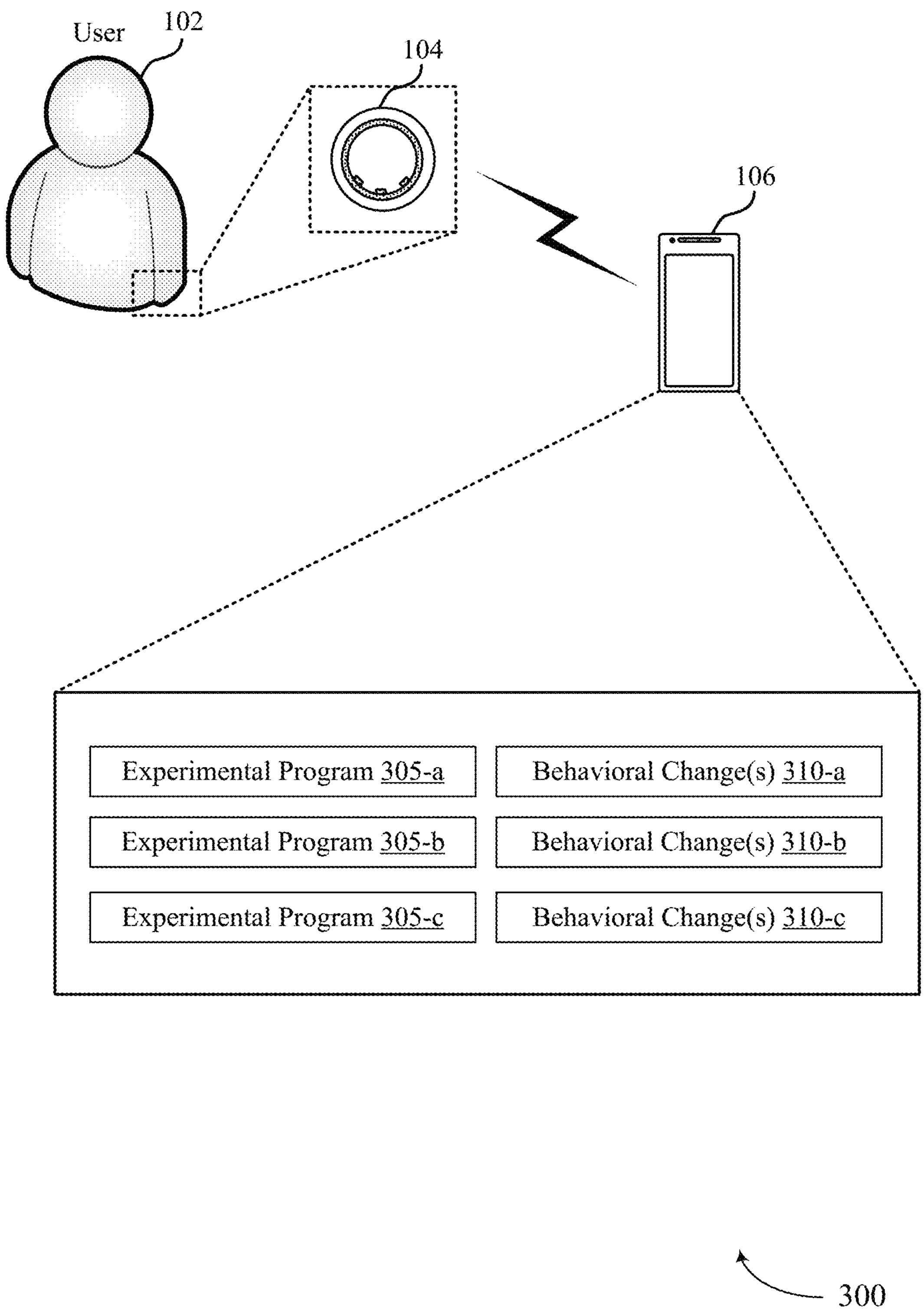
FIG. 3 illustrates an example of a system that supports techniques for experimental programs using data from wearable devices in accordance with aspects of the present disclosure.

FIG. 3 illustrates an example of a system 300 that supports techniques for experimental programs using data from wearable devices in accordance with aspects of the present disclosure. Aspects of the system 300 may implement, or may be implemented by, aspects of the system 100, the system 200, or both. For example, the system 300 may support techniques that enable users to participate in experimental programs to adjust one or more aspects of their overall health, as described herein.

The system 300 includes a user 102, a wearable device 104 (e.g., wearable ring device 104), and a user device 106, that may be examples of corresponding devices as described in FIGS. 1 and 2. In some aspects, the system 300 may enable the user 102 to subscribe to, or otherwise participate in, one or more experimental programs 305 associated with behavioral changes 310 that are intended to adjust one or more aspects of the user's overall health. Behavioral changes 310 associated with the respective experimental programs 305 may include, but are not limited to, behavioral changes associated with caffeine consumption (e.g., amount and/or timing of caffeine consumption), exercise (e.g., amount, type, and/or timing of exercise), a stretching or meditation regimen, a supplement regimen (e.g., vitamin regimen), food/alcohol consumption (e.g., amount, type, and/or timing of food/alcohol consumption), a sleep pattern (e.g., amount and/or timing of sleep, sleeping conditions), and the like.

In some cases, the system 300 may automatically recommend experimental programs 305 to the user 102 based on the user's physiological data and/or health/fitness goals. In other cases, the user 102 may search for different experimental programs 305 that are intended to and/or have been proven to affect certain health-related parameters or characteristics of the user 102. Furthermore, in some cases, the user 102 may be able to design their own experimental programs 305 including different behavioral changes 310, where the system 300 is configured to determine how (and/or to what extent) the experimental program 305 has on the user's physiological health.

For example, referring to the system 300, the wearable device 104 may acquire PPG data from the user using the one or more light-emitting components and one or more light-receiving components. The wearable device 104 may acquire baseline physiological data from the user throughout a time interval. The baseline physiological data may include baseline data for various physiological parameters, such as baseline heart rate data, baseline HRV data, baseline respiratory rate data, baseline blood oxygen saturation data, baseline PPG data, and the like. Additionally, or alternatively, the baseline physiological data may include baseline data associated with one or more scores calculated for the user 102 (e.g., baseline Sleep Score, baseline Readiness Score, baseline Activity Score), and/or contributors for the respective scores (e.g., baseline sleep efficiency data, baseline sleep latency data, and the like).

In some aspects, the system 300 may recommend (e.g., via a GUI of the user device 106) one or more experimental programs 305 to the user based on the user's baseline physiological data. For example, if the user's baseline physiological data indicates that the user 102 is getting poor sleep, the system 300 may recommend experimental programs 305 that may improve the user's overall sleep. In additional or alternative implementations, the user 102 may manually search for different experimental programs 305 (e.g., see what experimental programs 305 their friends are participating or have participated in), be recommended experimental programs from other users 102, and the like.

Additionally, or alternatively, the system 300 may recommend experimental programs 305 based on a user input received from the user 102. For example, the user 102 may indicate (e.g., via the user device 106) that they want to improve their sleep efficiency. In this example, the system 300 may recommend experimental programs 305 that may improve the user's sleep efficiency. For instance, the system 300 may recommend a first experimental program 305-*a* in which participating users 102 refrain from consuming caffeine for six hours before bedtime (e.g., behavioral change 310-*a* is refraining from consuming caffeine). By way of another example, the system 300 may recommend a second experimental program 305-*b* in which participating users 102 refrain from eating food for four hours before bedtime (e.g., behavioral change 310-*b* is refraining from consuming food), and a third experimental program 305-*c* in which participating users 102 reduce screen time for two hours before bedtime (e.g., behavioral change 310-*c* is reducing screen time).

In some cases, the system 300 may select which experimental programs 305 to recommend from a database of experimental programs 305 (that may be maintained at the user device 106, servers 110, etc.). The system 300 may select which experimental programs 305 to recommend based on the user's baseline physiological (e.g., PPG) data, the user's health/fitness goals (that may be inputted via the user device 106), the user's bibliographic information (e.g., age, gender, weight, body type, etc.), based on what experimental programs 305 resulted in positive changes for other users 106 (e.g., other users with similar goals, baseline data, and/or bibliographic information), and the like. In this regard, the system 300 may be configured to evaluate what types of experimental programs 305 resulted in positive health-related changes for similar users 102, and may therefore recommend such experimental programs 305 to the user 102.

In some aspects, the system 300 may be configured to calculate or estimate one or more estimated parameter changes associated with the respective experimental programs 305, where the estimated parameter changes indicate estimated changes in physiological parameters of the user's baseline PPG data that may result from the respective experimental programs 305. For example, if the user 102 wants to improve their sleep efficiency, the system 300 may indicate that the first experimental program 305-*a* is expected/estimated to improve the user's sleep efficiency by X %. Similarly, the system 300 may indicate that the second experimental program 305-*b* and the third experimental program 305-*c* are expected/estimated to improve the user's sleep efficiency by Y % and Z %, respectively. In some cases, the order that the experimental programs 305 are recommended/displayed to the user 102 may be based on the estimated parameter changes of the respective experimental programs 305.

The system 300 may calculate/determine the estimated parameter changes on one or more physiological parameters for the respective experimental programs 305 based on any number of factors, including the user's baseline physiological (e.g., PPG) data, expected/predicted adherence rates to the experimental programs 305 (e.g., whether the user 102 fully adheres to the experimental program 305, or only adheres to the experimental program 305 50% of the time, etc.), based on how the experimental program affected physiological parameters for other users 102, and the like. For example, the system 300 may indicate that the first experimental program 305-*a* resulted in X % increased sleep efficiency for other users 102 of the same sex and similar weight/age. In some implementations, the system 300 may utilize machine learning techniques (e.g., machine learning classifiers/algorithms) to determine estimated parameter changes.

For example, the system 300 may input the baseline PPG data into the machine learning classifier. In such cases, in response to inputting the baseline PPG data into the machine learning classifier, the system 300 may select one or more experimental programs from a plurality of experimental programs. In some cases, the system 300 may input the additional PPG data into the machine learning classifier, and identify the adherence to the behavioral change in response to (e.g., after) inputting the additional PPG data into the machine learning classifier.

In some cases, each experimental program 305 may be associated with one or more targeted physiological parameters. For the purposes of the present disclosure, the term "targeted physiological parameters" may include physiological parameters that are monitored and tracked throughout the experimental program 305. For example, targeted physiological parameters for an experimental program 305 in which user's refrain from consuming alcohol may include sleep efficiency and heart rate, whereas targeted physiological parameters for an experimental program 305 in which user's refrain from consuming caffeine may include sleep latency and respiration rate. In cases where the user 102 creates their own experimental program 305, the system 300 may be configured to identify physiological parameters that change the most throughout the program as the targeted physiological parameters (which will then be displayed to the user throughout and/or after the end of the experimental program 305).

Similarly, each experimental program 305 may be associated with a respective time interval/duration. The time interval/duration of each respective experimental program 305 may be based on the corresponding behavioral change(s) 310, the targeted physiological parameters, based on experiences/feedback of other users who participated in the experimental program 305, and the like. For example, an experimental program 305 associated with a behavioral change 310 in which users adjust their sleep schedule may be associated with a longer time interval (e.g., longer time before users notice changes) as compared to an experimental program associated with a behavioral change 310 in which users refrain from consuming alcohol (that may take less time before users notice changes).

In some aspects, user device 106 may display information or instructions associated with the respective experimental programs 305, such as the time interval/duration of the programs, instructions for adhering to the associated behavioral changes 310, estimated parameter changes (e.g., how the user's data is expected to change), how different adherence levels may affect the user's results, how other users reacted/responded (e.g., feedback) to the respective programs, and the like.

Subsequently, the user 102 may elect to participate in an experimental program 305. For example, upon being recommended the experimental programs 305-*a*, 305-*b*, and 305-*b*, the user 102 may select to participate in the first experimental program 305.

Upon selecting/electing to participate in an experimental program 305, the wearable device 104 may continue collecting additional physiological data (e.g., PPG data heart rate, HRV, respiration rate, blood oxygen saturation, Sleep Score, Readiness Score, sleep efficiency, sleep latency, etc.) from the user throughout a time interval of the experimental program 305.

In some aspects, the system 300 may be configured to determine a level of adherence of the user 102 to the behavioral change 310 associated with the selected experimental program 305. For example, if the user elects to participate in an experimental program 305 in which participating users 102 refrain from drinking alcohol for two weeks, the system 300 may determine the user's level of adherence based on whether or not (or how much/how frequently) the user consumes alcohol during the two weeks of the experimental program 305. In this example, the more the user 102 consumes alcohol, the lower the level of adherence. Conversely, the less the user 102 consumes alcohol, the higher the level of adherence (where no alcohol consumption may be "perfect" adherence).

In some implementations, the system 300 may determine the user's level of adherence based on additional physiological data collected by the wearable device 104 throughout the experimental program 305. In some cases, the additional physiological data may be an example of additional PPG data. In particular, the system 300 may be configured to perform gesture recognition and/or recognize patterns in the user's physiological data in order to determine if/when the user is engaging (or has engaged) in certain activities. For example, acceleration/motion data collected via the wearable device 104 may be used to perform gesture recognition for drinking-related gestures, and may therefore be used to determine a relative probability that the user has consumed alcohol (and therefore adherence level). In additional or alternative implementations, the user's level of adherence may be determined based on measured physiological data (e.g., changes in PPG, heart rate, HRV, glucose, hemoglobin, fat level, respiratory rate, etc.) without gesture and/or location data. In such cases, the system 300 may "learn" how the user's baseline parameters change (short-term) after eating fatty food or drinking alcohol, and may therefore detect similar changes (e.g., changes in heart rate, HRV, etc.) to determine when a user has eaten fatty food or consumed alcohol.

For instance, if the system 300 identifies a drinking gesture, and determines that the user's heart rate and respiration rate increased following the drinking gesture, the system 300 may be configured to determine that the user consumed alcohol. In this example, the system 300 may automatically "tag" alcohol consumption (e.g., within the wearable application 250), and may determine the user's adherence to the behavioral change 310 (e.g., refraining from alcohol consumption) based on tagging the alcohol consumption.

Other sources of information may be used to determine the user's adherence level to respective behavioral changes 310, such as location data for the user, user inputs (e.g., "tags") received via the wearable device 104 and/or user device 106, and the like. For example, continuing with the example above, the user 102 may utilize the wearable device 104 and/or the user device to manually 106 tag alcohol consumption, where the tags may be used to determine adherence to the experimental program 305. By way of another example, if location data for the user 102 indicates that the user 102 was at a bar, and the system 300 identifies drinking-related gestures while the user 102 was at the bar, the system 300 may automatically tag alcohol consumption, that may be used to determine the user's level of adherence.

In cases where the system 300 automatically generates tags or identifies events that the user 102 participated in (e.g., alcohol consumption, food consumption, caffeine consumption, a workout, etc.), the user 102 may be able to confirm/deny the tag/activity via the user device 106.

Moreover, the user may manually be able to input tags via the wearable device 104 (e.g., via pre-determined tapping patterns or rotating patterns performed on the wearable device 106) and/or the user device 106. In other cases, near-field communications (NFC) chips may be used to facilitate input of tags. For example, an NFC chip may be placed on or near the user's coffee maker, such that when the user taps the NFC chip with the user device 106 and/or wearable device 104, the wearable application 250 automatically "tags" a cup of coffee.

The system 300 may be configured to display messages or alerts to the user 102 associated with the selected experimental program 305, such as information associated with the user's determined level of adherence to the behavioral change 310 of the experimental program 305. For example, if the system 300 determines a high level of adherence (e.g., the user is consistently making the behavioral change 310), the user device 106 may display a message congratulating the user 102 on their efforts, and encouraging the user 102 to keep it up. By way of another example, if the system 300 determines a low level of adherence (e.g., the user is failing to make the behavioral change 310), the user device 106 may display a message acknowledging the lack of adherence, but encouraging the user 102 to stick with the experimental program 305.

In some cases, the system 300 may display information indicating how varying levels of adherence throughout the remainder of the experimental program 305 may positively or negatively affect the user 102. For example, the system 300 may display a message that states: "If you completely refrain from consuming alcohol through the remainder of the program, we expect your sleep efficiency to increase by X %." By way of another example, the system 300 may display a message that states: "If you reduce your caffeine consumption after noon for 5 of the remaining 7 days of the program, we expect your sleep efficiency to increase by Y %." Such messages may help improve the user's adherence, and improve the completion rate of experimental programs 305

In some aspects, the user device 106 may display information associated with the experimental program 305 throughout the duration of the experimental program 305, after a conclusion of the experimental program 305, or both. For example, in cases where the user 102 is participating in an experimental program 305 associated with reduced caffeine consumption (behavioral change 310), the user device 106 may display a graph that indicates the user's sleep efficiency on days that the user 102 consumed caffeine compared to the days that the user 102 did not consume caffeine.

By displaying changes in the user's physiological data in real time, or near-real time, techniques described herein may enable users to visually see the impact that behavioral changes 310 have on their physiological data and overall health. As such, techniques described herein may improve adherence to behavioral changes 310, improve a completion rate of experimental programs 305, and help users make long-lasting behavioral changes 310 to improve their overall health.

By way of another example, after the conclusion of the experimental program 305, the user device 106 may display a summary report that summarizes changes to the user's physiological data (e.g., targeted physiological parameters) relative to their baseline over the course of the experimental program 305. For example, in the context of an experimental program 305 for adjusting a timing of meals, the user device 106 may display a summary report indicating how targeted physiological parameters for the experimental program 305 (e.g., resting heart rate, sleep efficiency, and sleep latency) changed over the course of the experimental program 305. In some cases, the user 102 may be able to recommend or suggest one or more modifications to the experimental program 305, such as via user inputs inputted via the user device 106.

Figure 4:
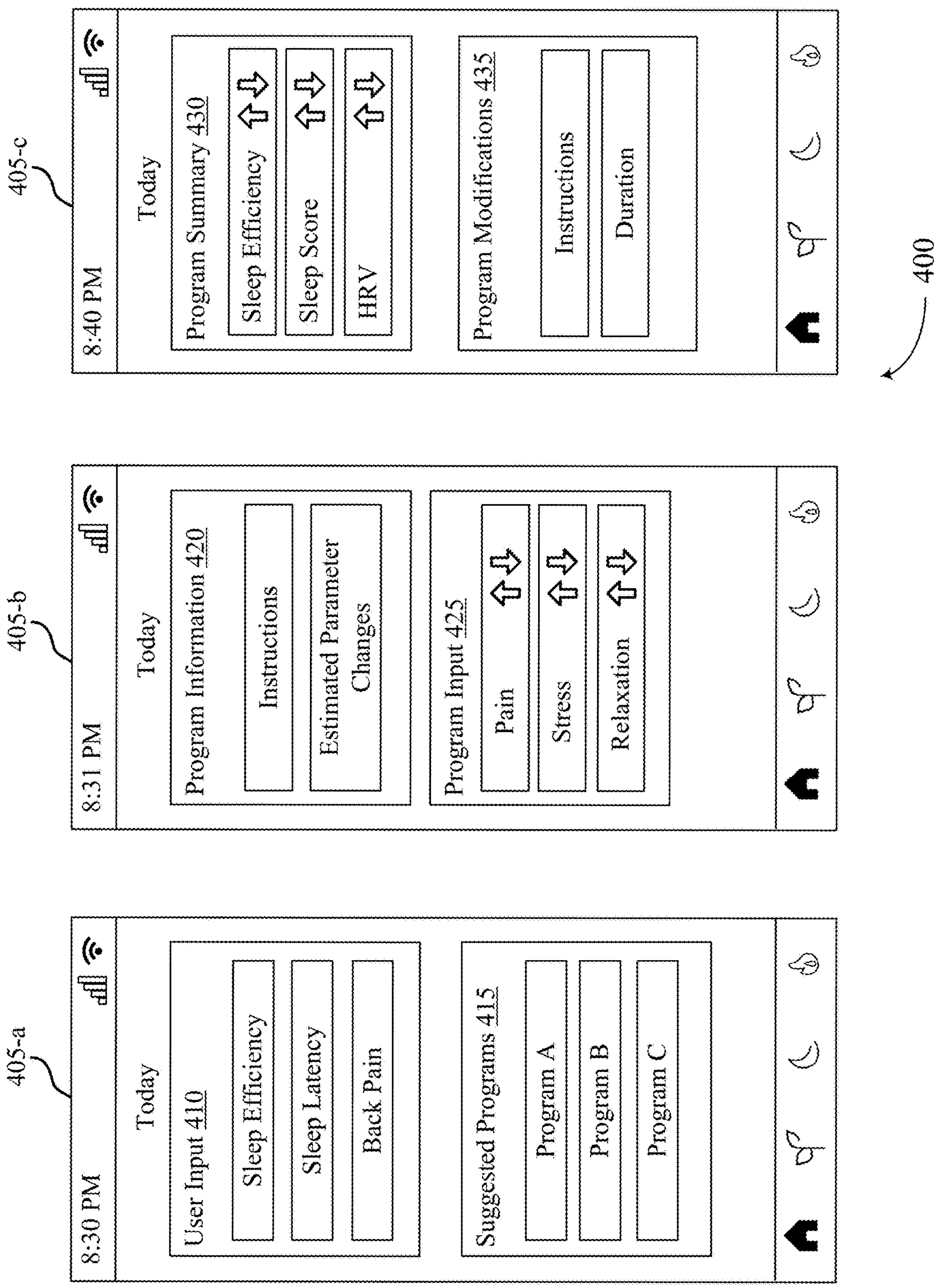
FIG. 4 illustrates an example of a graphical user interface (GUI) that supports techniques for experimental programs using data from wearable devices in accordance with aspects of the present disclosure.

FIG. 4 illustrates an example of a GUI 400 that supports techniques for experimental programs using data from wearable devices in accordance with aspects of the present disclosure. The GUI 400 may implement, or be implemented by, aspects of the system 100, the system 200, the system 300, or any combination thereof. For example, the GUI 400 may include an example of the GUI included within a user device 106.

The GUI 400 illustrates a series of application pages 405 that may be displayed to the user via the GUI 400 (e.g., GUI 275 illustrated in FIG. 2). The first application page 405-*a* may display a user input prompt 410 that provides different options of physiological parameters that the user may wish to change or improve. For example, the user may wish to improve their sleep efficiency, their sleep latency, reduce back pain, and the like.

User inputs received via the user input prompt 410 may be used to recommend suggested programs 415. Additionally, or alternatively, as described herein, the system may automatically recommend experimental programs (e.g., suggested programs 415) based on baseline physiological data acquired from the user. For example, if the system determines that the user is suffering from poor sleep quality based on baseline physiological data acquired from the wearable device 104, the system may recommend suggested programs 415 (e.g., suggested experimental programs) including Experimental Programs A, B, and C, that are configured/intended to improve the user's sleep quality/efficiency.

In some aspects, the suggested programs 415 may indicate estimated parameter changes for the respective experimental programs (e.g., how much, or to what extent, the respective experimental programs are expected/forecasted to change one more physiological parameters). Displaying estimated parameter changes for the respective experimental programs may enable the user to choose which program to participate in.

Upon selecting an experimental program to participate in, the second application page 405-*b* may display program information 420 associated with the respective experimental program. Program information 420 may include, but is not limited to, instructions for participating/adhering to the experimental program, estimated parameter changes, how the program affected physiological parameters for other users, a duration of the experimental program, and the like.

In some cases, the second application page 405-*b* may include a program input prompt 425 where the user can input different subjective feelings or other information (e.g., tags, such as tags for activities that the user has engaged in) associated with the experimental program. For example, the program input prompt 425 may include options for indicating the relative pain, stress, and/or relaxation felt by the user throughout the experimental program. Additionally, or alternatively, the program input prompt 425 may include options that enable the user to input "tags" associated with activities performed by the user (e.g., caffeine consumption, alcohol consumption, exercise, etc.). As noted previously herein, the user may also be able to input tags via the wearable device 104 (e.g., predetermined tapping patterns to input tags), via voice controls for the user device 106 and/or other devices such as Siri, Google, etc., and the like. Such inputted tags may be used to determine adherence to the experimental program.

The third application page 405-*c* may include a program summary 430 that may be displayed during and/or after completion of the experimental program. The program summary 430 may indicate whether various health metrics for the user have improved/changed over the course of the experimental program. For instance, the program summary 430 may indicate whether the sleep efficiency, the Sleep Score, and/or the HRV of the user has changed over the course of the experimental program (e.g., based on a comparison of baseline physiological (e.g., PPG) data acquired prior to the experimental program compared to physiological (e.g., PPG) data acquired during/after the experimental program). By way of another example, the program summary 430 may display information regarding how the user's physiological data was affected on days that the user did or did not adhere to the experimental program.

The third application page 405-*c* may also display one or more program modifications 435 for the experimental program. The program modifications 435 may include a change in one or more parameters/characteristics of the experimental program, such as instructions for performing the experimental program, a duration of the program, and the like. Additionally, or alternatively, the program modifications 435 may enable the user to provide feedback regarding the experimental program (e.g., whether the user would/would not recommend the program, ratings/reviews for the program, etc.).

In some implementations, the application pages 405 of the GUI may display only the user's own information as they participate in the experimental program. In additional or alternative implementations, the application pages 405 may also enable the user to see information (e.g., physiological data, parameter changes) associated with other users who are participating (or have participated in) the experimental program.

Figure 5:
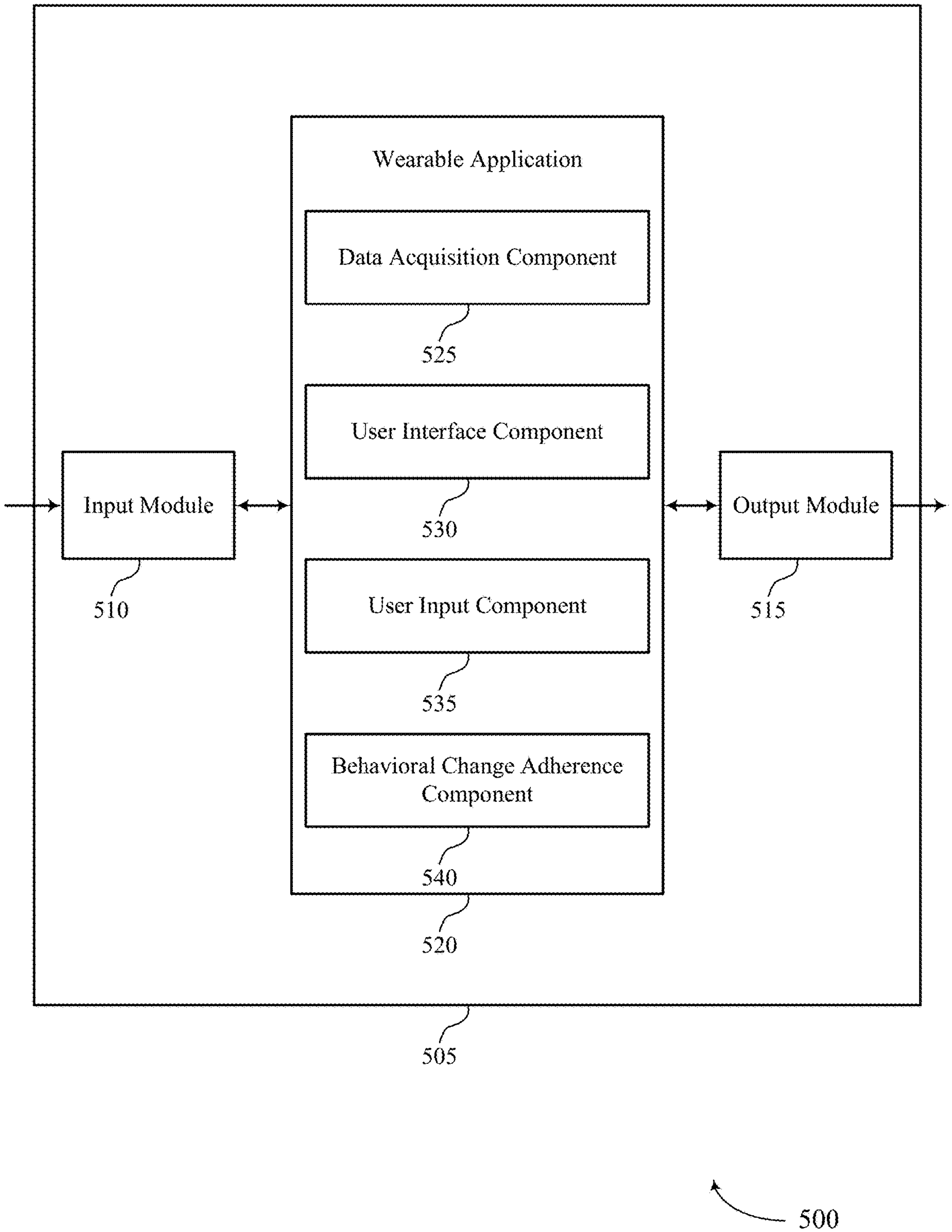
FIG. 5 shows a block diagram of an apparatus that supports techniques for experimental programs using data from wearable devices in accordance with aspects of the present disclosure.

FIG. 5 shows a block diagram 500 of a device 505 that supports techniques for experimental programs using data from wearable devices in accordance with aspects of the present disclosure. The device 505 may include an input module 510, an output module 515, and a wearable application 520. The device 505 may also include a processor. Each of these components may be in communication with one another (e.g., via one or more buses).

The input module 510 may provide a means for receiving information such as packets, user data, control information, or any combination thereof associated with various information channels (e.g., control channels, data channels, information channels related to illness detection techniques). Information may be passed on to other components of the device 505. The input module 510 may utilize a single antenna or a set of multiple antennas.

The output module 515 may provide a means for transmitting signals generated by other components of the device 505. For example, the output module 515 may transmit information such as packets, user data, control information, or any combination thereof associated with various information channels (e.g., control channels, data channels, information channels related to illness detection techniques). In some examples, the output module 515 may be co-located with the input module 510 in a transceiver module. The output module 515 may utilize a single antenna or a set of multiple antennas.

For example, the wearable application 520 may include a data acquisition component 525, a user interface component 530, a user input component 535, a behavioral change adherence component 540, or any combination thereof. In some examples, the wearable application 520, or various components thereof, may be configured to perform various operations (e.g., receiving, monitoring, transmitting) using or otherwise in cooperation with the input module 510, the output module 515, or both. For example, the wearable application 520 may receive information from the input module 510, send information to the output module 515, or be integrated in combination with the input module 510, the output module 515, or both to receive information, transmit information, or perform various other operations as described herein.

The data acquisition component 525 may be configured as or otherwise support a means for acquiring, using a wearable device, PPG data from a user using one or more light-emitting components and one or more light-receiving components. The data acquisition component 525 may be configured as or otherwise support a means for acquiring, using the wearable device, baseline physiological data from the user throughout a time interval, the baseline physiological data comprising baseline PPG data collected by the wearable device using the one or more light-emitting components and the one or more light-receiving components. The user interface component 530 may be configured as or otherwise support a means for causing a GUI of a user device to display one or more experimental programs, the one or more experimental programs selected from a plurality of experimental programs based at least in part on the baseline PPG data, wherein each of the plurality of experimental programs is associated with one or more behavioral changes. The user input component 535 may be configured as or otherwise support a means for receiving, via the user device, a selection of an experimental program from the one or more experimental programs. The data acquisition component 525 may be configured as or otherwise support a means for acquiring additional physiological data from the user via the wearable device for at least a portion of a second time interval associated with the experimental program. The behavioral change adherence component 540 may be configured as or otherwise support a means for identifying adherence of the user to a behavioral change associated with the experimental program based at least in part on the additional PPG data, information received via the user device, or both. The user interface component 530 may be configured as or otherwise support a means for causing the GUI of the user device to display information associated with the experimental program based at least in part on identifying the adherence to the behavioral change, wherein the information comprises one or more changes between the baseline PPG data and the additional PPG data.

Figure 6:
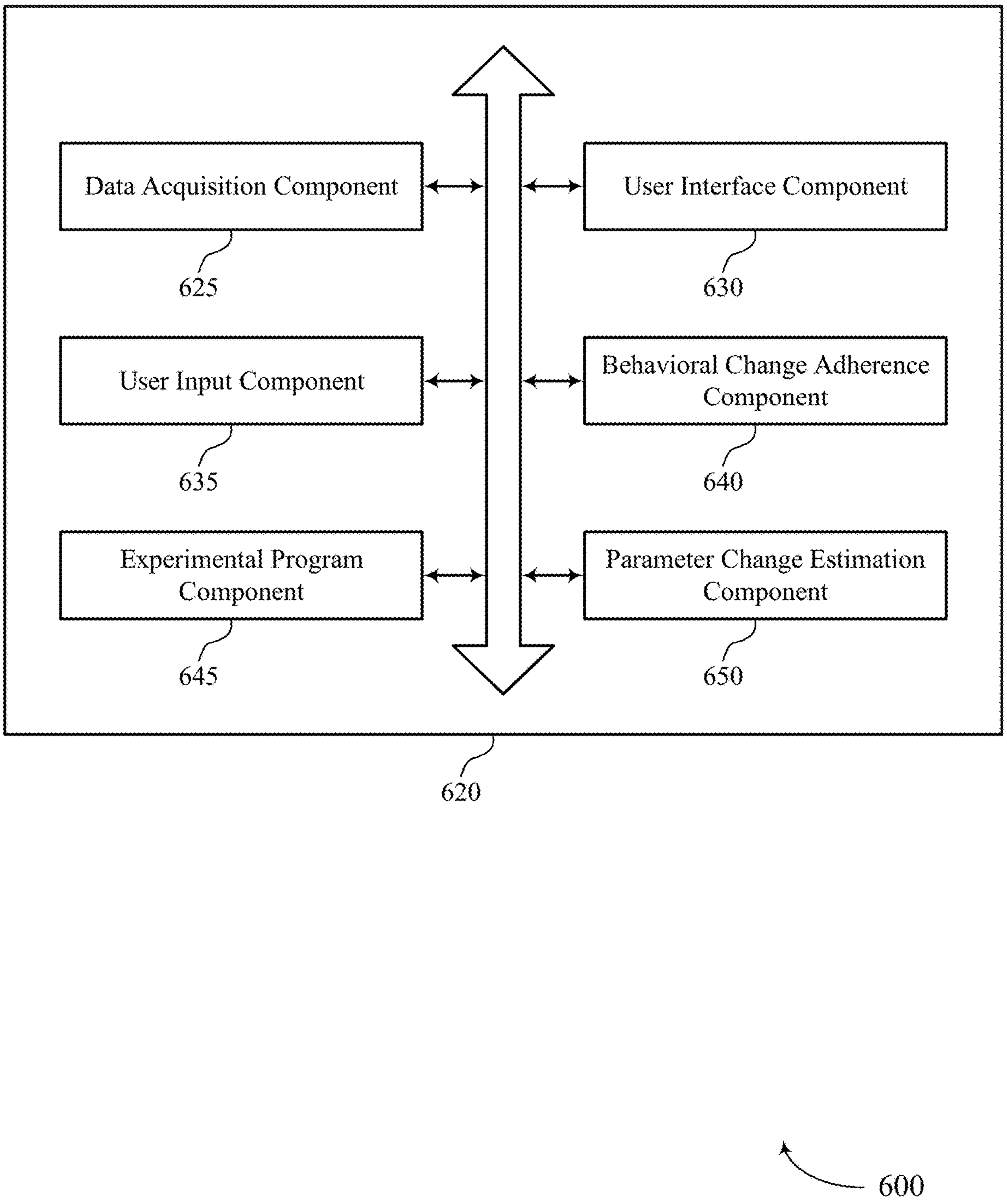
FIG. 6 shows a block diagram of a wearable application that supports techniques for experimental programs using data from wearable devices in accordance with aspects of the present disclosure.

FIG. 6 shows a block diagram 600 of a wearable application 620 that supports techniques for experimental programs using data from wearable devices in accordance with aspects of the present disclosure. The wearable application 620 may be an example of aspects of a wearable application or a wearable application 520, or both, as described herein. The wearable application 620, or various components thereof, may be an example of means for performing various aspects of techniques for experimental programs using data from wearable devices as described herein. For example, the wearable application 620 may include a data acquisition component 625, a user interface component 630, a user input component 635, a behavioral change adherence component 640, an experimental program component 645, a parameter change estimation component 650, or any combination thereof. Each of these components may communicate, directly or indirectly, with one another (e.g., via one or more buses).

The data acquisition component 625 may be configured as or otherwise support a means for acquiring, using a wearable device, PPG data from a user using one or more light-emitting components and one or more light-receiving components. The data acquisition component 625 may be configured as or otherwise support a means for acquiring, using the wearable device, baseline physiological data from the user throughout a time interval, the baseline physiological data comprising baseline PPG data collected by the wearable device using the one or more light-emitting components and the one or more light-receiving components. The user interface component 630 may be configured as or otherwise support a means for causing a GUI of a user device to display one or more experimental programs, the one or more experimental programs selected from a plurality of experimental programs based at least in part on the baseline PPG data, wherein each of the plurality of experimental programs is associated with one or more behavioral changes. The user input component 635 may be configured as or otherwise support a means for receiving, via the user device, a selection of an experimental program from the one or more experimental programs. In some examples, the data acquisition component 625 may be configured as or otherwise support a means for acquiring additional PPG data from the user via the wearable device for at least a portion of a second time interval associated with the experimental program. The behavioral change adherence component 640 may be configured as or otherwise support a means for identifying adherence of the user to a behavioral change associated with the experimental program based at least in part on the additional PPG data, information received via the user device, or both. In some examples, the user interface component 630 may be configured as or otherwise support a means for causing the GUI of the user device to display information associated with the experimental program based at least in part on identifying the adherence to the behavioral change, wherein the information comprises one or more changes between the baseline PPG data and the additional PPG data.

In some examples, the user input component 635 may be configured as or otherwise support a means for receiving, from the user device, a user input indicating one or more physiological parameters associated with the baseline PPG data that the user wants to change. In some examples, the experimental program component 645 may be configured as or otherwise support a means for selecting the one or more experimental programs from the plurality of experimental programs based at least in part on the one or more physiological parameters.

In some examples, the user interface component 630 may be configured as or otherwise support a means for causing the GUI of the user device to display one or more estimated parameter changes associated with the one or more experimental programs, the one or more estimated parameter changes indicating estimated changes in the one or more physiological parameters that are based at least in part on the respective one or more experimental programs.

In some examples, the parameter change estimation component 650 may be configured as or otherwise support a means for determining the one or more estimated parameter changes based at least in part on the baseline PPG data and based at least in part on PPG data acquired from a plurality of other users that have participated in the one or more experimental programs. In some examples, the information received via the user device comprises location information, taggable events inputted via the user device, or both.

In some examples, the user interface component 630 may be configured as or otherwise support a means for causing the GUI to display one or more messages associated with the experimental program based at least in part on identifying the adherence of the user to the behavioral change.

In some examples, the data acquisition component 625 may be configured as or otherwise support a means for identifying one or more activities the user engaged in throughout at least a portion of the experimental program based at least in part on the additional PPG data, location data associated with the user, or both, wherein identifying the adherence to the behavioral change is based at least in part on the one or more activities.

In some examples, the user input component 635 may be configured as or otherwise support a means for receiving, from the user device, a user input indicating biographical information associated with the user, wherein the one or more experimental programs are selected based at least in part on the biographical information, and wherein the biographical information comprises an age, a gender, a body type, a health or fitness goal, or any combination thereof.

In some examples, the behavioral change associated with the experimental program is associated with caffeine consumption, food consumption, alcohol consumption, screen time, exercise, a sleeping pattern, or any combination thereof.

In some examples, the user interface component 630 may be configured as or otherwise support a means for causing the GUI of the user device to display additional information associated with a plurality of additional users that have participated in the experimental program, wherein the additional information comprises one or more additional changes between baseline PPG data for the plurality of additional users and PPG data collected from the plurality of additional users throughout the experimental program.

In some examples, the wearable device comprises a wearable ring device. In some examples, the baseline PPG data, the additional PPG data, or both, is acquired by the wearable device based on arterial blood flow, capillary blood flow, arteriole blood flow, or a combination thereof.

Figure 7:
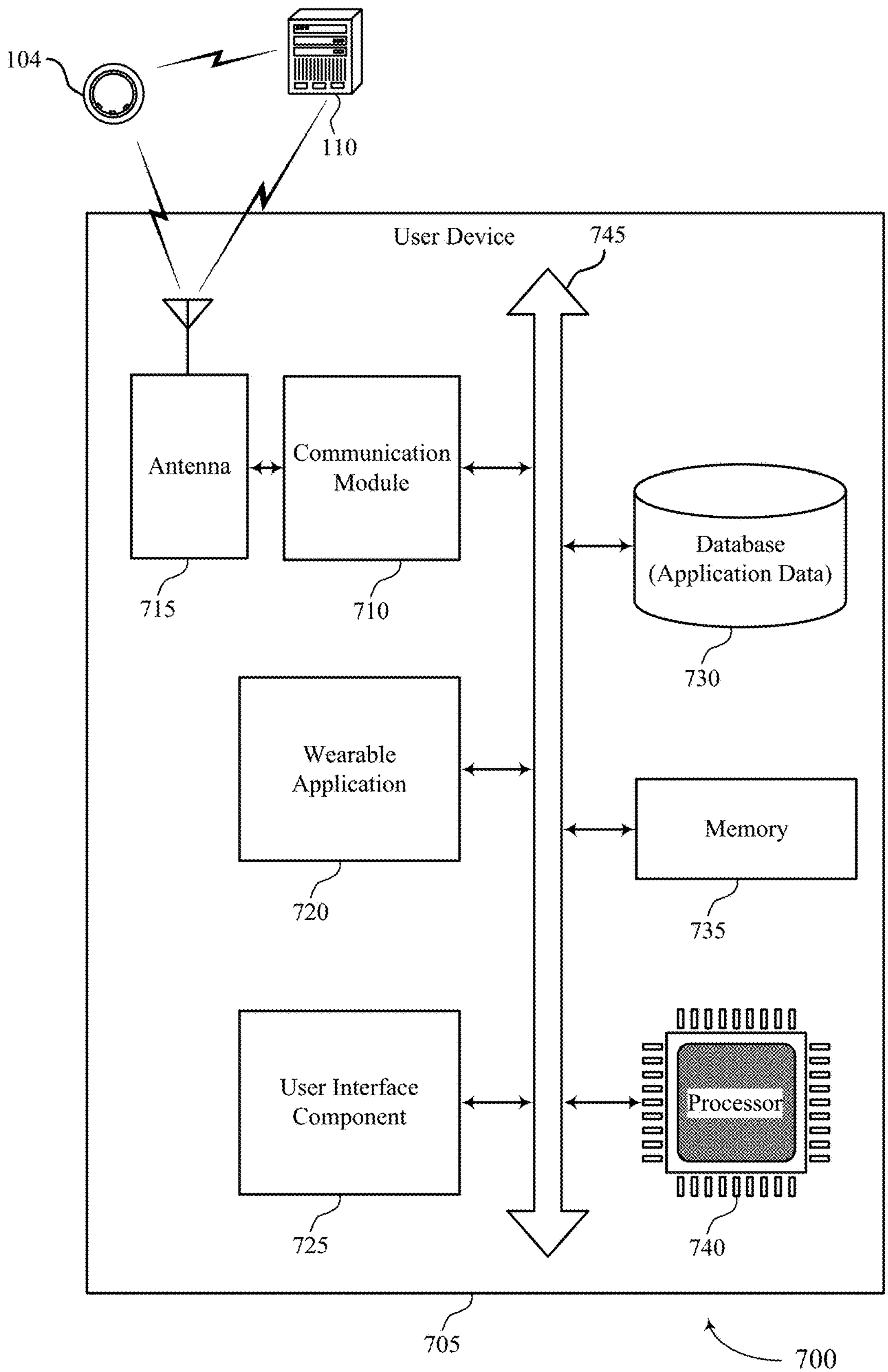
FIG. 7 shows a diagram of a system including a device that supports techniques for experimental programs using data from wearable devices in accordance with aspects of the present disclosure.

FIG. 7 shows a diagram of a system 700 including a device 705 that supports techniques for experimental programs using data from wearable devices in accordance with aspects of the present disclosure. The device 705 may be an example of or include the components of a device 505 as described herein. The device 705 may include an example of a user device 106, as described previously herein. The device 705 may include components for bi-directional communications including components for transmitting and receiving communications with a wearable device 104 and a server 110, such as a wearable application 720, a communication module 710, an antenna 715, a user interface component 725, a database (application data) 730, a memory 735, and a processor 740. These components may be in electronic communication or otherwise coupled (e.g., operatively, communicatively, functionally, electronically, electrically) via one or more buses (e.g., a bus 745).

The communication module 710 may manage input and output signals for the device 705 via the antenna 715. The communication module 710 may include an example of the communication module 220-*b* of the user device 106 shown and described in FIG. 2. In this regard, the communication module 710 may manage communications with the ring 104 and the server 110, as illustrated in FIG. 2. The communication module 710 may also manage peripherals not integrated into the device 705. In some cases, the communication module 710 may represent a physical connection or port to an external peripheral. In some cases, the communication module 710 may utilize an operating system such as iOS®, ANDROID®, MS-DOS®, MS-WINDOWS®, OS/2®, UNIX®, LINUX®, or another known operating system. In other cases, the communication module 710 may represent or interact with a wearable device (e.g., ring 104), modem, a keyboard, a mouse, a touchscreen, or a similar device. In some cases, the communication module 710 may be implemented as part of the processor 740. In some examples, a user may interact with the device 705 via the communication module 710, user interface component 725, or via hardware components controlled by the communication module 710.

In some cases, the device 705 may include a single antenna 715. However, in some other cases, the device 705 may have more than one antenna 715, that may be capable of concurrently transmitting or receiving multiple wireless transmissions. The communication module 710 may communicate bi-directionally, via the one or more antennas 715, wired, or wireless links as described herein. For example, the communication module 710 may represent a wireless transceiver and may communicate bi-directionally with another wireless transceiver. The communication module 710 may also include a modem to modulate the packets, to provide the modulated packets to one or more antennas 715 for transmission, and to demodulate packets received from the one or more antennas 715.

The user interface component 725 may manage data storage and processing in a database 730. In some cases, a user may interact with the user interface component 725. In other cases, the user interface component 725 may operate automatically without user interaction. The database 730 may be an example of a single database, a distributed database, multiple distributed databases, a data store, a data lake, or an emergency backup database.

The memory 735 may include RAM and ROM. The memory 735 may store computer-readable, computer-executable software including instructions that, when executed, cause the processor 740 to perform various functions described herein. In some cases, the memory 735 may contain, among other things, a BIOS that may control basic hardware or software operation such as the interaction with peripheral components or devices.

The processor 740 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 740 may be configured to operate a memory array using a memory controller. In other cases, a memory controller may be integrated into the processor 740. The processor 740 may be configured to execute computer-readable instructions stored in a memory 735 to perform various functions (e.g., functions or tasks supporting a method and system for sleep staging algorithms).

For example, the wearable application 720 may be configured as or otherwise support a means for acquiring, using a wearable device, PPG data from a user using one or more light-emitting components and one or more light-receiving components and acquiring, using the wearable device, baseline physiological data from a user via a wearable device throughout a time interval, the baseline physiological data comprising baseline PPG data collected by the wearable device using the one or more light-emitting components and the one or more light-receiving components. The wearable application 720 may be configured as or otherwise support a means for causing a GUI of a user device to display one or more experimental programs, the one or more experimental programs selected from a plurality of experimental programs based at least in part on the baseline PPG data, wherein each of the plurality of experimental programs is associated with one or more behavioral changes. The wearable application 720 may be configured as or otherwise support a means for receiving, via the user device, a selection of an experimental program from the one or more experimental programs. The wearable application 720 may be configured as or otherwise support a means for acquiring additional PPG data from the user via the wearable device for at least a portion of a second time interval associated with the experimental program. The wearable application 720 may be configured as or otherwise support a means for identifying adherence of the user to a behavioral change associated with the experimental program based at least in part on the additional PPG data, information received via the user device, or both. The wearable application 720 may be configured as or otherwise support a means for causing the GUI of the user device to display information associated with the experimental program based at least in part on identifying the adherence to the behavioral change, wherein the information comprises one or more changes between the baseline PPG data and the additional PPG data.

The wearable application 720 may include an application (e.g., "app"), program, software, or other component that is configured to facilitate communications with a ring 104, server 110, other user devices 106, and the like. For example, the wearable application 720 may include an application executable on a user device 106 that is configured to receive data (e.g., physiological data) from a ring 104, perform processing operations on the received data, transmit and receive data with the servers 110, and cause presentation of data to a user 102.

Figure 8:
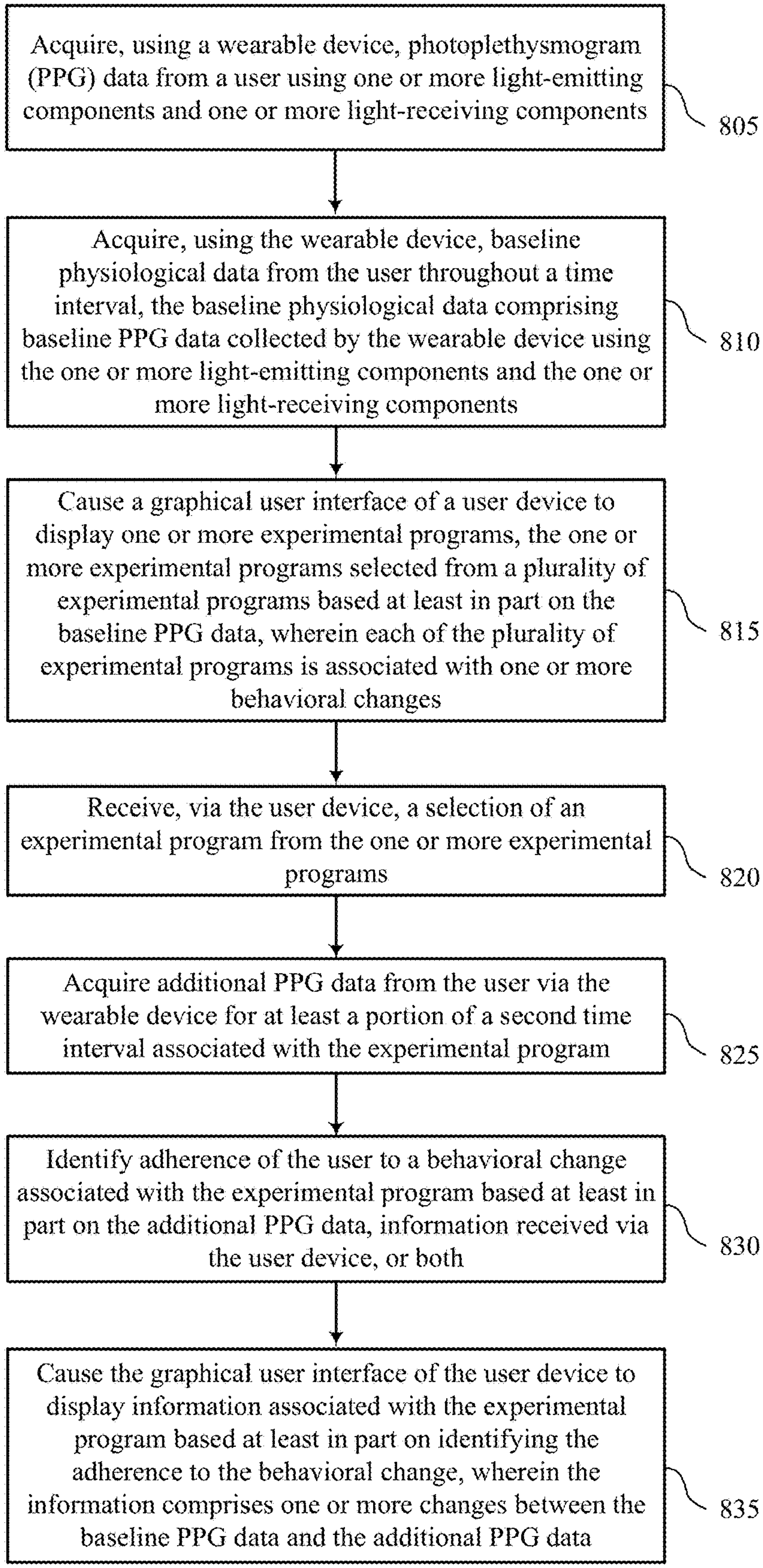
FIGS. 8 through 9 show flowcharts illustrating methods that support techniques for experimental programs using data from wearable devices in accordance with aspects of the present disclosure.

FIG. 8 shows a flowchart illustrating a method 800 that supports techniques for experimental programs using data from wearable devices in accordance with aspects of the present disclosure. The operations of the method 800 may be implemented by a user device or its components as described herein. For example, the operations of the method 800 may be performed by a user device as described with reference to FIGS. 1 through 7. In some examples, a user device may execute a set of instructions to control the functional elements of the user device to perform the described functions. Additionally, or alternatively, the user device may perform aspects of the described functions using special-purpose hardware.

At 805, the method may include acquiring, using a wearable device, PPG data from a user using one or more light-emitting components and one or more light-receiving components. The operations of 805 may be performed in accordance with examples as disclosed herein. In some examples, aspects of the operations of 805 may be performed by a data acquisition component 625 as described with reference to FIG. 6.

At 810, the method may include acquiring, using the wearable device, baseline physiological data from the user throughout a time interval, the baseline physiological data comprising baseline PPG data collected by the wearable device using the one or more light-emitting components and the one or more light-receiving components. The operations of 810 may be performed in accordance with examples as disclosed herein. In some examples, aspects of the operations of 810 may be performed by a data acquisition component 625 as described with reference to FIG. 6.

At 815, the method may include causing a GUI of a user device to display one or more experimental programs, the one or more experimental programs selected from a plurality of experimental programs based at least in part on the baseline PPG data, wherein each of the plurality of experimental programs is associated with one or more behavioral changes. The operations of 815 may be performed in accordance with examples as disclosed herein. In some examples, aspects of the operations of 815 may be performed by a user interface component 630 as described with reference to FIG. 6.

At 820, the method may include receiving, via the user device, a selection of an experimental program from the one or more experimental programs. The operations of 820 may be performed in accordance with examples as disclosed herein. In some examples, aspects of the operations of 820 may be performed by a user input component 635 as described with reference to FIG. 6.

At 825, the method may include acquiring additional PPG data from the user via the wearable device for at least a portion of a second time interval associated with the experimental program. The operations of 825 may be performed in accordance with examples as disclosed herein. In some examples, aspects of the operations of 825 may be performed by a data acquisition component 625 as described with reference to FIG. 6.

At 830, the method may include identifying adherence of the user to a behavioral change associated with the experimental program based at least in part on the additional PPG data, information received via the user device, or both. The operations of 830 may be performed in accordance with examples as disclosed herein. In some examples, aspects of the operations of 830 may be performed by a behavioral change adherence component 640 as described with reference to FIG. 6.

At 835, the method may include causing the GUI of the user device to display information associated with the experimental program based at least in part on identifying the adherence to the behavioral change, wherein the information comprises one or more changes between the baseline PPG data and the additional PPG data. The operations of 835 may be performed in accordance with examples as disclosed herein. In some examples, aspects of the operations of 835 may be performed by a user interface component 630 as described with reference to FIG. 6.

Figure 9:
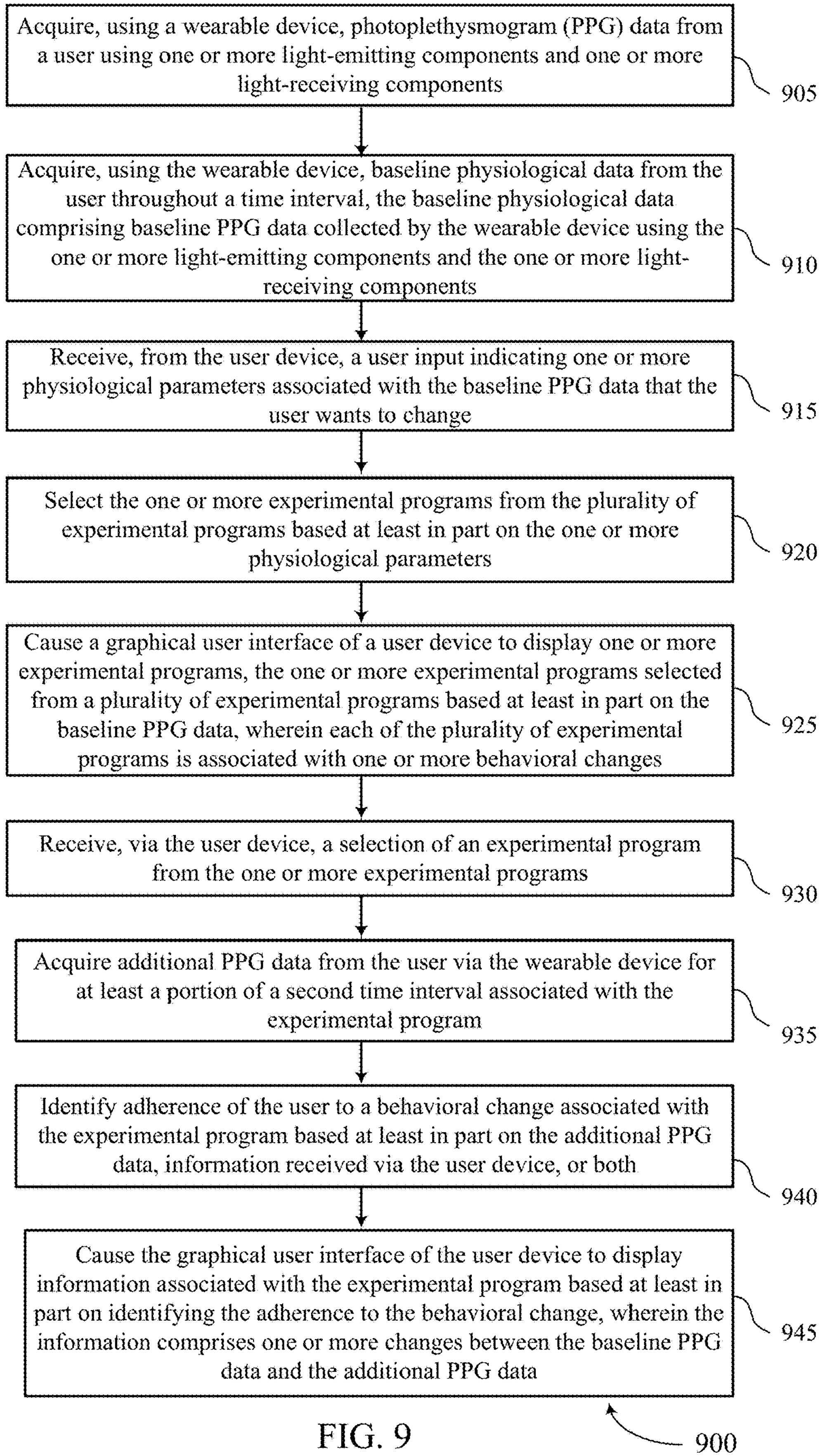

FIG. 9 shows a flowchart illustrating a method 900 that supports techniques for experimental programs using data from wearable devices in accordance with aspects of the present disclosure. The operations of the method 900 may be implemented by a user device or its components as described herein. For example, the operations of the method 900 may be performed by a user device as described with reference to FIGS. 1 through 7. In some examples, a user device may execute a set of instructions to control the functional elements of the user device to perform the described functions. Additionally, or alternatively, the user device may perform aspects of the described functions using special-purpose hardware.

At 905, the method may include acquiring, using a wearable device, PPG data from a user using one or more light-emitting components and one or more light-receiving components. The operations of 905 may be performed in accordance with examples as disclosed herein. In some examples, aspects of the operations of 905 may be performed by a data acquisition component 625 as described with reference to FIG. 6.

At 910, the method may include acquiring, using the wearable device, baseline physiological data from the user throughout a time interval, the baseline physiological data comprising baseline PPG data collected by the wearable device using the one or more light-emitting components and the one or more light-receiving components. The operations of 910 may be performed in accordance with examples as disclosed herein. In some examples, aspects of the operations of 910 may be performed by a data acquisition component 625 as described with reference to FIG. 6.

At 915, the method may include receiving, from the user device, a user input indicating one or more physiological parameters associated with the baseline PPG data that the user wants to change. The operations of 915 may be performed in accordance with examples as disclosed herein. In some examples, aspects of the operations of 915 may be performed by a user input component 635 as described with reference to FIG. 6.

At 920, the method may include selecting the one or more experimental programs from a plurality of experimental programs based at least in part on the one or more physiological parameters. The operations of 920 may be performed in accordance with examples as disclosed herein. In some examples, aspects of the operations of 920 may be performed by an experimental program component 645 as described with reference to FIG. 6.

At 925, the method may include causing a GUI of a user device to display the one or more experimental programs, the one or more experimental programs selected from a plurality of experimental programs based at least in part on the baseline PPG data, wherein each of the plurality of experimental programs is associated with one or more behavioral changes. The operations of 925 may be performed in accordance with examples as disclosed herein. In some examples, aspects of the operations of 925 may be performed by a user interface component 630 as described with reference to FIG. 6.

At 930, the method may include receiving, via the user device, a selection of an experimental program from the one or more experimental programs. The operations of 930 may be performed in accordance with examples as disclosed herein. In some examples, aspects of the operations of 930 may be performed by a user input component 635 as described with reference to FIG. 6.

At 935, the method may include acquiring additional PPG data from the user via the wearable device for at least a portion of a second time interval associated with the experimental program. The operations of 935 may be performed in accordance with examples as disclosed herein. In some examples, aspects of the operations of 935 may be performed by a data acquisition component 625 as described with reference to FIG. 6.

At 940, the method may include identifying adherence of the user to a behavioral change associated with the experimental program based at least in part on the additional PPG data, information received via the user device, or both. The operations of 940 may be performed in accordance with examples as disclosed herein. In some examples, aspects of the operations of 940 may be performed by a behavioral change adherence component 640 as described with reference to FIG. 6.

At 945, the method may include causing the GUI of the user device to display information associated with the experimental program based at least in part on identifying the adherence to the behavioral change, wherein the information comprises one or more changes between the baseline PPG data and the additional PPG data. The operations of 945 may be performed in accordance with examples as disclosed herein. In some examples, aspects of the operations of 945 may be performed by a user interface component 630 as described with reference to FIG. 6.

It should be noted that the methods described above describe possible implementations, and that the operations and the steps may be rearranged or otherwise modified and that other implementations are possible. Furthermore, aspects from two or more of the methods may be combined.

A method is described. The method may include acquiring, using a wearable device, PPG data from a user using one or more light-emitting components and one or more light-receiving components, acquiring, using the wearable device, baseline physiological data from the user throughout a time interval, the baseline physiological data comprising baseline PPG data collected by the wearable device using the one or more light-emitting components and the one or more light-receiving components, causing a GUI of a user device to display one or more experimental programs, the one or more experimental programs selected from a plurality of experimental programs based at least in part on the baseline PPG data, wherein each of the plurality of experimental programs is associated with one or more behavioral changes, receiving, via the user device, a selection of an experimental program from the one or more experimental programs, acquiring additional PPG data from the user via the wearable device for at least a portion of a second time interval associated with the experimental program, identifying adherence of the user to a behavioral change associated with the experimental program based at least in part on the additional PPG data, information received via the user device, or both, and causing the GUI of the user device to display information associated with the experimental program based at least in part on identifying the adherence to the behavioral change, wherein the information comprises one or more changes between the baseline PPG data and the additional PPG data.

A system is described. The system may include a wearable device configured to acquire PPG data from a user using one or more light-emitting components and one or more light-receiving components, a user device communicatively coupled to the wearable device, the user device configured to execute an application associated with the wearable device, and one or more processors communicatively coupled with the wearable device and the user device, wherein the one or more processors are configured to acquire, using a wearable device, PPG data from a user using the one or more light-emitting components and one or more light-receiving components, acquire, using the wearable device, baseline physiological data from the user throughout a time interval, the baseline physiological data comprising baseline PPG data collected by the wearable device using the one or more light-emitting components and the one or more light-receiving components, cause a GUI of a user device to display one or more experimental programs, the one or more experimental programs selected from a plurality of experimental programs based at least in part on the baseline PPG data, wherein each of the plurality of experimental programs is associated with one or more behavioral changes, receive, via the user device, a selection of an experimental program from the one or more experimental programs, acquire additional PPG data from the user via the wearable device for at least a portion of a second time interval associated with the experimental program, identify adherence of the user to a behavioral change associated with the experimental program based at least in part on the additional PPG data, information received via the user device, or both, and cause the GUI of the user device to display information associated with the experimental program based at least in part on identifying the adherence to the behavioral change, wherein the information comprises one or more changes between the baseline PPG data and the additional PPG data.

An apparatus is described. The apparatus may include a processor, memory coupled with the processor, and instructions stored in the memory. The instructions may be executable by the processor to cause the apparatus to acquire, using a wearable device, PPG data from a user using one or more light-emitting components and one or more light-receiving components, acquire, using the wearable device, baseline physiological data from the user throughout a time interval, the baseline physiological data comprising baseline PPG data collected by the wearable device using the one or more light-emitting components and the one or more light-receiving components, cause a GUI of a user device to display one or more experimental programs, the one or more experimental programs selected from a plurality of experimental programs based at least in part on the baseline PPG data, wherein each of the plurality of experimental programs is associated with one or more behavioral changes, receive, via the user device, a selection of an experimental program from the one or more experimental programs, acquire additional PPG data from the user via the wearable device for at least a portion of a second time interval associated with the experimental program, identify adherence of the user to a behavioral change associated with the experimental program based at least in part on the additional PPG data, information received via the user device, or both, and cause the GUI of the user device to display information associated with the experimental program based at least in part on identifying the adherence to the behavioral change, wherein the information comprises one or more changes between the baseline PPG data and the additional PPG data.

Another apparatus is described. The apparatus may include means for acquiring, using a wearable device, PPG data from a user using one or more light-emitting components and one or more light-receiving components, means for acquiring, using the wearable device, baseline physiological data from the user throughout a time interval, the baseline physiological data comprising baseline PPG data collected by the wearable device using the one or more light-emitting components and the one or more light-receiving components, means for causing a GUI of a user device to display one or more experimental programs, the one or more experimental programs selected from a plurality of experimental programs based at least in part on the baseline PPG data, wherein each of the plurality of experimental programs is associated with one or more behavioral changes, means for receiving, via the user device, a selection of an experimental program from the one or more experimental programs, means for acquiring additional PPG data from the user via the wearable device for at least a portion of a second time interval associated with the experimental program, means for identifying adherence of the user to a behavioral change associated with the experimental program based at least in part on the additional PPG data, information received via the user device, or both, and means for causing the GUI of the user device to display information associated with the experimental program based at least in part on identifying the adherence to the behavioral change, wherein the information comprises one or more changes between the baseline PPG data and the additional PPG data.

A non-transitory computer-readable medium storing code is described. The code may include instructions executable by a processor to acquire, using a wearable device, PPG data from a user using one or more light-emitting components and one or more light-receiving components, acquire, using the wearable device, baseline physiological data from the user throughout a time interval, the baseline physiological data comprising baseline PPG data collected by the wearable device using the one or more light-emitting components and the one or more light-receiving components, cause a GUI of a user device to display one or more experimental programs, the one or more experimental programs selected from a plurality of experimental programs based at least in part on the baseline PPG data, wherein each of the plurality of experimental programs is associated with one or more behavioral changes, receive, via the user device, a selection of an experimental program from the one or more experimental programs, acquire additional PPG data from the user via the wearable device for at least a portion of a second time interval associated with the experimental program, identify adherence of the user to a behavioral change associated with the experimental program based at least in part on the additional PPG data, information received via the user device, or both, and cause the GUI of the user device to display information associated with the experimental program based at least in part on identifying the adherence to the behavioral change, wherein the information comprises one or more changes between the baseline PPG data and the additional PPG data.

Some examples of the method, systems, apparatuses, and non-transitory computer-readable medium described herein may further include operations, features, means, or instructions for receiving, from the user device, a user input indicating one or more physiological parameters associated with the baseline PPG data that the user wants to change and selecting the one or more experimental programs from the plurality of experimental programs based at least in part on the one or more physiological parameters.

Some examples of the method, systems, apparatuses, and non-transitory computer-readable medium described herein may further include operations, features, means, or instructions for causing the GUI of the user device to display one or more estimated parameter changes associated with the one or more experimental programs, the one or more estimated parameter changes indicating estimated changes in the one or more physiological parameters that may be based at least in part on the respective one or more experimental programs.

Some examples of the method, systems, apparatuses, and non-transitory computer-readable medium described herein may further include operations, features, means, or instructions for determining the one or more estimated parameter changes based at least in part on the baseline PPG data and based at least in part on PPG data acquired from a plurality of other users that may have participated in the one or more experimental programs.

In some examples of the method, systems, apparatuses, and non-transitory computer-readable medium described herein, the information received via the user device comprises location information, taggable events inputted via the user device, or both.

Some examples of the method, systems, apparatuses, and non-transitory computer-readable medium described herein may further include operations, features, means, or instructions for causing the GUI to display one or more messages associated with the experimental program based at least in part on identifying the adherence of the user to the behavioral change.

Some examples of the method, systems, apparatuses, and non-transitory computer-readable medium described herein may further include operations, features, means, or instructions for identifying one or more activities the user engaged in throughout at least a portion of the experimental program based at least in part on the additional PPG data, location data associated with the user, or both, wherein identifying the adherence to the behavioral change may be based at least in part on the one or more activities.

Some examples of the method, systems, apparatuses, and non-transitory computer-readable medium described herein may further include operations, features, means, or instructions for receiving, from the user device, a user input indicating biographical information associated with the user, wherein the one or more experimental programs may be selected based at least in part on the biographical information, and wherein the biographical information comprises an age, a gender, a body type, a health or fitness goal, or any combination thereof.

In some examples of the method, systems, apparatuses, and non-transitory computer-readable medium described herein, the behavioral change associated with the experimental program may be associated with caffeine consumption, food consumption, alcohol consumption, screen time, exercise, a sleeping pattern, or any combination thereof.

Some examples of the method, systems, apparatuses, and non-transitory computer-readable medium described herein may further include operations, features, means, or instructions for causing the GUI of the user device to display additional information associated with a plurality of additional users that may have participated in the experimental program, wherein the additional information comprises one or more additional changes between baseline PPG data for the plurality of additional users and PPG data collected from the plurality of additional users throughout the experimental program.

In some examples of the method, systems, apparatuses, and non-transitory computer-readable medium described herein, the wearable device comprises a wearable ring device.

In some examples of the method, systems, apparatuses, and non-transitory computer-readable medium described herein, the baseline PPG data, the additional PPG data, or both, may be acquired by the wearable device based on arterial blood flow, capillary blood flow, arteriole blood flow, or a combination thereof.

Some examples of the method, systems, apparatuses, and non-transitory computer-readable medium described herein may further include operations, features, means, or instructions for inputting the baseline PPG data into a machine learning classifier, wherein the one or more experimental programs selected from a plurality of experimental programs is based at least in part on inputting the baseline PPG data into the machine learning classifier.

Some examples of the method, systems, apparatuses, and non-transitory computer-readable medium described herein may further include operations, features, means, or instructions for inputting the additional PPG data into a machine learning classifier, wherein identifying the adherence to the behavioral change is based at least in part on inputting the additional PPG data into the machine learning classifier.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A system, comprising:

a wearable device configured to acquire photoplethysmogram (PPG) data from a user using one or more light-emitting components and one or more light-receiving components;

a user device communicatively coupled to the wearable device, the user device configured to execute an application associated with the wearable device; and one or more processors communicatively coupled with the wearable device and the user device, wherein the one or more processors are configured to:

acquire, using the wearable device, baseline physiological data from the user throughout a time interval, the baseline physiological data comprising baseline PPG data collected by the wearable device using the one or more light-emitting components and the one or more light-receiving components;

acquire, at the user device and from the wearable device, the baseline PPG data collected by the wearable device;

cause a graphical user interface of the user device to display one or more experimental programs, the one or more experimental programs selected from a plurality of experimental programs based at least in part on the baseline PPG data, wherein each of the plurality of experimental programs is associated with one or more behavioral changes;

receive, via the user device, a selection of an experimental program from the one or more experimental programs;

acquire additional PPG data from the user via the wearable device for at least a portion of a second time interval associated with the experimental program;

acquire, at the user device and from the wearable device, the additional PPG data;

identify adherence of the user to a behavioral change associated with the experimental program based at least in part on the additional PPG physiological data, information received via the user device, or both; and cause the graphical user interface of the user device to display information associated with the experimental program based at least in part on identifying the adherence to the behavioral change, wherein the information comprises one or more changes between the baseline PPG data and the additional PPG data.

2. The system of claim 1, wherein the one or more processors are further configured to:

receive, from the user device, a user input indicating one or more physiological parameters associated with the baseline PPG data that the user wants to change; and select the one or more experimental programs from the plurality of experimental programs based at least in part on the one or more physiological parameters.

3. The system of claim 2, wherein the one or more processors are further configured to:

cause the graphical user interface of the user device to display one or more estimated parameter changes associated with the one or more experimental programs, the one or more estimated parameter changes indicating estimated changes in the one or more physiological parameters that are based at least in part on the one or more experimental programs.

4. The system of claim 3, wherein the one or more processors are further configured to:

determine the one or more estimated parameter changes based at least in part on the baseline PPG data and based at least in part on PPG data acquired from a plurality of other users that have participated in the one or more experimental programs.

5. The system of claim 1, wherein the one or more processors are further configured to:

input the baseline PPG data into a machine learning classifier, wherein the one or more experimental programs are from the plurality of experimental programs based at least in part on inputting the baseline PPG data into the machine learning classifier.

6. The system of claim 1, wherein the one or more processors are further configured to:

input the additional PPG data into a machine learning classifier, wherein identifying the adherence to the behavioral change is based at least in part on inputting the additional PPG data into the machine learning classifier.

7. The system of claim 1, wherein the information received via the user device comprises location information, taggable events inputted via the user device, or both.

8. The system of claim 1, wherein the one or more processors are further configured to:

cause the graphical user interface to display one or more messages associated with the experimental program based at least in part on identifying the adherence of the user to the behavioral change.

9. The system of claim 1, wherein the one or more processors are further configured to:

identify one or more activities the user engaged in throughout at least a portion of the experimental program based at least in part on the additional PPG data, location data associated with the user, or both, wherein identifying the adherence to the behavioral change is based at least in part on the one or more activities.

10. The system of claim 1, wherein the one or more processors are further configured to:

receive, from the user device, a user input indicating biographical information associated with the user, wherein the one or more experimental programs are selected based at least in part on the biographical information, and wherein the biographical information comprises an age, a gender, a body type, a health or fitness goal, or any combination thereof.

11. The system of claim 1, wherein the behavioral change associated with the experimental program is associated with caffeine consumption, food consumption, alcohol consumption, screen time, exercise, a sleeping pattern, or any combination thereof.

12. The system of claim 1, wherein the one or more processors are further configured to:

cause the graphical user interface of the user device to display additional information associated with a plurality of additional users that have participated in the experimental program, wherein the additional information comprises one or more additional changes between baseline PPG data for the plurality of additional users and PPG data collected from the plurality of additional users throughout the experimental program.

13. The system of claim 1, wherein the wearable device comprises a wearable ring device.

14. The system of claim 1, wherein the baseline PPG data, the additional PPG data, or both, is acquired by the wearable device based on arterial blood flow, capillary blood flow, arteriole blood flow, or a combination thereof.

15. A method, comprising:

acquiring, using a wearable device, photoplethysmogram (PPG) data from a user using one or more light-emitting components and one or more light-receiving components;

acquiring, using the wearable device, baseline physiological data from the user throughout a time interval, the baseline physiological data comprising baseline PPG data collected by the wearable device using the one or more light-emitting components and the one or more light-receiving components;

acquiring, at a user device and from the wearable device, the baseline PPG data collected by the wearable device;

causing a graphical user interface of a user device to display one or more experimental programs, the one or more experimental programs selected from a plurality of experimental programs based at least in part on the baseline PPG data, wherein each of the plurality of experimental programs is associated with one or more behavioral changes;

receiving, via the user device, a selection of an experimental program from the one or more experimental programs;

acquiring additional PPG data from the user via the wearable device for at least a portion of a second time interval associated with the experimental program;

acquiring, at the user device and from the wearable device, the additional PPG data;

identifying adherence of the user to a behavioral change associated with the experimental program based at least in part on the additional PPG data, information received via the user device, or both; and causing the graphical user interface of the user device to display information associated with the experimental program based at least in part on identifying the adherence to the behavioral change, wherein the information comprises one or more changes between the baseline PPG data and the additional PPG data.

16. The method of claim 15, further comprising:

receiving, from the user device, a user input indicating one or more physiological parameters associated with the baseline PPG data that the user wants to change; and selecting the one or more experimental programs from the plurality of experimental programs based at least in part on the one or more physiological parameters.

17. The method of claim 16, further comprising:

causing the graphical user interface of the user device to display one or more estimated parameter changes associated with the one or more experimental programs, the one or more estimated parameter changes indicating estimated changes in the one or more physiological parameters that are based at least in part on the one or more experimental programs.

18. The method of claim 17, further comprising:

determining the one or more estimated parameter changes based at least in part on the baseline PPG data and based at least in part on PPG data acquired from a plurality of other users that have participated in the one or more experimental programs.

19. The method of claim 15, wherein the information received via the user device comprises location information, taggable events inputted via the user device, or both.

20. A non-transitory computer-readable medium storing code, the code comprising instructions executable by a processor to:

acquire, using a wearable device, photoplethysmogram (PPG) data from a user using one or more light-emitting components and one or more light-receiving components;

acquire, using the wearable device, baseline physiological data from the user throughout a time interval, the baseline physiological data comprising baseline PPG data collected by the wearable device using the one or more light-emitting components and the one or more light-receiving components;

acquire, at a user device and from the wearable device, the baseline PPG data collected by the wearable device;

cause a graphical user interface of a user device to display one or more experimental programs, the one or more experimental programs selected from a plurality of experimental programs based at least in part on the baseline PPG data, wherein each of the plurality of experimental programs is associated with one or more behavioral changes;

receive, via the user device, a selection of an experimental program from the one or more experimental programs;

acquire additional PPG data from the user via the wearable device for at least a portion of a second time interval associated with the experimental program;

acquire, at the user device and from the wearable device, the additional PPG data;

identify adherence of the user to a behavioral change associated with the experimental program based at least in part on the additional PPG data, information received via the user device, or both; and cause the graphical user interface of the user device to display information associated with the experimental program based at least in part on identifying the adherence to the behavioral change, wherein the information comprises one or more changes between the baseline PPG data and the additional PPG data.

* * * * *